(12) United States Patent
Svensby (10) Patent No.: US 10,772,999 B2
(45) Date of Patent: Sep. 15, 2020

(54) WOUND DRESSINGS

(71) Applicant: Mölnlycke Health Care AB, Gothenburg (SE)

(72) Inventor: Anna Svensby, Västra Frölunda (SE)

(73) Assignee: MÖLNLYCKE HEALTH CARE AB, Gothenburg (SE)

( * ) Notice: Subject to any disclaimer, the term of this patent is extended or adjusted under 35 U.S.C. 154(b) by 450 days.

(21) Appl. No.: 15/525,107

(22) PCT Filed: Nov. 16, 2015

(86) PCT No.: PCT/EP2015/076648
§ 371 (c)(1),
(2) Date: May 8, 2017

(87) PCT Pub. No.: WO2016/079037
PCT Pub. Date: May 26, 2016

(65) Prior Publication Data
US 2017/0312406 A1    Nov. 2, 2017

(30) Foreign Application Priority Data
Nov. 20, 2014  (EP) .................................... 14194054

(51) Int. Cl.
*A61F 13/00* (2006.01)
*A61M 1/00* (2006.01)
*A61F 13/02* (2006.01)

(52) U.S. Cl.
CPC ..... *A61M 1/0088* (2013.01); *A61F 13/00068* (2013.01); *A61F 13/022* (2013.01); *A61F 13/0216* (2013.01); *A61M 1/0023* (2013.01)

(58) Field of Classification Search
CPC combination set(s) only.
See application file for complete search history.

(56) References Cited

U.S. PATENT DOCUMENTS

| | | | | |
|---|---|---|---|---|
| 3,814,095 A | * | 6/1974 | Lubens | A61K 9/703 604/307 |
| 5,330,452 A | * | 7/1994 | Zook | A61K 9/703 424/447 |
| 9,572,962 B2 | | 2/2017 | Scholz | |

(Continued)

FOREIGN PATENT DOCUMENTS

| | | |
|---|---|---|
| CN | 101547712 A | 9/2009 |
| CN | 102046120 A | 5/2011 |

(Continued)

OTHER PUBLICATIONS

European Search Report and Written Opinion dated May 28, 2015 by the European Patent Office for EP Application No. 14194054.4, which was filed on Nov. 20, 2014 and published as EP 3023083 A1 on May 25, 2016 (Applicant-Mölnlycke Health Care AB) (5 pages).

(Continued)

*Primary Examiner* — Ariana Zimbouski
(74) *Attorney, Agent, or Firm* — Ballard Spahr LLP (57) ABSTRACT

A wound dressing comprises a wound pad and a backing layer on a non-wound facing side of the backing layer. At least a portion of a sealing ring is provided within 5 mm of and continuously along the contour of the wound pad. A negative pressure wound treatment system comprising such a wound dressing is also disclosed.

17 Claims, 8 Drawing Sheets

(56) References Cited

U.S. PATENT DOCUMENTS

| | | | |
|---|---|---|---|
| 2002/0156410 A1* | 10/2002 | Lawry | A61F 13/0203 602/48 |
| 2005/0209574 A1* | 9/2005 | Boehringer | A61F 13/00068 604/289 |
| 2006/0105028 A1* | 5/2006 | Zhang | A61F 13/063 424/448 |
| 2006/0228318 A1* | 10/2006 | Fabo | A61F 5/445 424/70.12 |
| 2007/0032754 A1* | 2/2007 | Walsh | A61M 1/0088 602/2 |
| 2014/0276490 A1 | 9/2014 | Locke et al. | |
| 2014/0277440 A1* | 9/2014 | Martin | A61F 2/12 623/8 |
| 2014/0330226 A1 | 11/2014 | Coffey | |
| 2016/0067107 A1* | 3/2016 | Cotton | A61L 15/28 602/44 |

FOREIGN PATENT DOCUMENTS

| | | |
|---|---|---|
| EP | 3023083 | 5/2016 |
| JP | H0956745 A | 3/1997 |
| WO | WO 2008/048527 | 4/2008 |
| WO | WO 2010/147533 | 12/2010 |
| WO | WO 2013/149078 | 10/2013 |

OTHER PUBLICATIONS

International Search Report and Written Opinion dated Jan. 20, 2016 by the International Searching Authority for International Application No. PCT/EP2015/076648, which was filed on Nov. 16, 2015 and published as WO 2016/079037 on May 26, 2016 (Applicant-Mölnlycke Health Care AB) (10 pages).

* cited by examiner

WOUND DRESSINGS

Cross-Reference to Related Applications

This application is a U.S. National Phase Application of International Application No. PCT/EP2015/076648, filed Nov. 16, 2015, which claims priority to European Application No. 14194054.4, filed Nov. 20, 2014, each of which are hereby incorporated by reference in their entirety.

BACKGROUND

Some wound dressings, typically known in the art as "border dressings," are comprised of an absorbent wound pad and a backing layer extending peripherally beyond the wound pad. Typically, such border wound dressings are affixed to a wound at adhesive "borders," at those parts of the backing layer (and/or corresponding parts of any additional layer(s)) that extend beyond the periphery of the wound pad.

Although such wound dressings are generally satisfactorily attached to body parts, in some instances, when wound dressings are applied to body parts that move (e.g. at joints) and/or rub against clothing or objects, the wound dressings may become partially detached from a wound site prematurely. Even partial detachment can compromise the function of the wound dressing—for example, by allowing wound exudate to leak out at the detached area(s) and/or by exposing the wound to the outside (therefore increasing the risk of infection from outside agents). Detached wound dressings may be difficult to re-apply, so they are often replaced with a new dressing, which can be costly.

In some applications, for example, in cases where the wound dressing is used as part of a negative pressure wound treatment system, it may be especially important that the wound dressing maintains an airtight seal over the wound.

SUMMARY

The present disclosure relates to improved wound dressings that exhibit, among other things, prolonged adherence to a wound site.

The present inventive concept is based on the insight that when prior art wound dressings are correctly applied to wounds and surrounding skin area, air pockets may be formed between border portions of the wound dressing and the skin. In particular, the inventor has realized that normally in such wound dressings (having a wound pad with a given thickness and a backing layer to be placed on the skin around the wound) the backing layer needs to be drawn towards the skin a distance which approximates the thickness of the wound pad. The material of the backing layer will generally be subjected to tension and will extend from the non-wound facing side of the wound pad obliquely towards skin, rather than straight down along the edge or contour of the wound pad, thus leaving an air pocket between the border portion (backing layer or other layer attached to the backing layer) and the skin. It is believed that formation of air pockets is particularly common for wound dressings having a soft adhesive, such as silicone. Providing a wound dressing with a stronger adhesive, such as comprising acrylate, may reduce the probability of air pockets forming, but strong adhesives have the disadvantage of lifting and thus irritating the skin, due to the tension of the border of the wound dressing.

The present inventive concept is also based on the insight that limiting the possibility of exudates to flow to areas of the wound dressing located peripherally of the wound pad can effectively reduce the risk of detachment of such peripheral areas. Without being bound by a particular theory, it is believed that by reducing the amount of exudates that can be accumulated in such peripheral areas (such as air pockets), the risk of detachment also becomes reduced, since a lower or no exudates volume will cause less wetting of the adhesive areas and/or less risk of pressure build-up between the skin and the wound dressing. The inventor has realized that this may be achieved by providing a sealing ring disposed close to the contour of the wound pad. This is reflected in at least a first aspect of the inventive concept.

Thus, according to a first aspect of the inventive concept, a wound dressing is provided. The wound dressing comprises
  a backing layer;
  a wound pad having a wound-facing side extending in a first geometrical plane, a non-wound facing side extending in a second geometrical plane, and a circumferential contour; and
  a sealing ring
wherein
the wound pad is affixed to the backing layer on the wound pad's non-wound facing side;
the backing layer extends beyond the periphery of the wound pad; and
at least a portion of the sealing ring is disposed:
between said first and said second plane,
within a distance of 5 mm from the contour of the wound pad, and
continuously along the contour of the wound pad.

By placing at least a portion of the sealing ring between the first and the second geometrical planes, the amount of exudates passing from the wound and into the wound pad and then into peripheral pockets between the skin and the wound dressing is reduced or avoided. If instead no portion of the sealing ring would be located between the first and the second geometrical planes, but instead on the wound-facing side of the wound pad, the risk of exudates leaking via the wound pad (avoiding the sealing ring) and into the peripheral pockets would be higher. It should be understood that, although at least a portion of the sealing ring is disposed within 5 mm of the contour of the wound pad, in at least some embodiments, other portions of the sealing ring may be located at a larger distance than 5 mm from the contour of the wound pad. In some exemplary embodiments, the entire sealing ring may be located within 5 mm of the contour of the wound pad.

It is believed that the formation of air pockets generally occur within 5 mm from the contour of the wound pad. The proximity of a portion of the sealing ring, within 5 mm of the contour of the wound pad is believed to effectively limit formation of said peripheral pockets and thus the amount of exudates gathering in such pockets, thereby reducing the risk of maceration and reducing the risk of the border loosening from the skin due to wetting and possibly due to build up of liquid pressure.

According to a second aspect of the inventive concept, a negative pressure wound treatment system is provided. The system comprises:
  a negative pressure source for providing negative pressure to a wound;
  a wound dressing in accordance with any embodiment of the first aspect; and a conduit configured to transmit negative pressure from the negative pressure source to the wound dressing.

BRIEF DESCRIPTION OF THE DRAWINGS

It will be appreciated that, depending on where a wound dressing is applied, it may be positioned in such a way that the underside shown in FIGS. 1-4 may be facing in other directions, e.g., upward, sideways. Unless otherwise noted, the terms "above," "below," "upper," "lower," "over," "under," "on top of," and similar references to position used in the description and in the claims refer to the relative location of various components with respect to one another when the dressing is in the situation shown in FIGS. 2 and 4.

FIG. 1 depicts cross sections of a prior art wound dressing. The prior art wound dressing is shown before it is applied to a wound in FIG. 1A.

FIG. 2 depicts cross sections of exemplary wound dressings of the present disclosure. An exemplary wound dressing is shown before it is applied to a wound in FIG. 2A.

FIG. 3 depicts cross sections of a prior art wound dressing having a wound contact layer. The prior art wound dressing is shown before it is applied to a wound in FIG. 3A. FIG. 3B depicts the present disclosure's proposed sketch of the wound dressing after it is applied to a wound.

FIG. 4 depicts cross sections of exemplary wound dressings of the present disclosure having wound contact layers. An exemplary wound dressing is shown before it is applied to a wound in FIG. 4A.

DEFINITIONS

As used herein, the term "hydrophilic" refers to the water-permeability property of a material or the water-attracting property of a molecule. In the context of a material with pores (such as, for example, open-cell foams) or materials with through-holes, such a material is "hydrophilic" if the material wicks up water. In the context of a material without pores or any through-holes, such a material is considered "hydrophilic" if it does not resist the flow of water into or through the material. For example, hydrophilicity of a material can be tested using a water column of up to one inch height exerting pressure on the material for at least 60 minutes, at least 90 minutes, or at least 24 hours. By "resisting," it is meant that any flow of water into or through the foam in such a test is below a detection limit for the test.

As used herein, the term "hydrophobic" refers to the water-impermeability property of a material or the water-repelling property of a molecule. In the context of a material with pores (such as, for example, open-cell foams) or materials with through-holes, such a material is "hydrophobic" if the material does not wick up water. In the context of a material without pores or any through-holes, such a material is considered "hydrophobic" if it resists the flow of water into or through the material. For example, hydrophobicity of a material can be tested using a water column of up to one inch height exerting pressure on the material for at least 60 minutes, at least 90 minutes, or at least 24 hours. By "resisting," it is meant that any flow of water into or through the foam in such a test is below a detection limit for the test.

As used herein, the terms "negative pressure," "vacuum," "suction," "reduced pressure," and "subatmospheric" are used interchangeably and all refer to pressure below normal atmospheric pressure.

As used herein, the term "sterilized" refers to 1) the state of being substantially free of living microorganisms, or 2) being subject to a process in order to be substantially free of living microorganisms.

As used herein, the term "wound", in addition to having its ordinary meaning in the medical arts, can refer to any body part of a patient (such as a human or animal) that one may desire to heal, protect from the elements, and/or subject to a course of treatment. The term also encompasses artificial wounds, for example, those created for the purposes of testing medical devices, studying wound healing, etc. The term encompasses, without limitation, traumatic wounds; wounds resulting from disease, pathogens, and/or irritants; and surgically created wounds.

As used herein, the term "wound site" refers to a wound together with any surrounding skin area where the dressing is attached/fixated to. The surrounding skin may or may not comprise healthy skin.

DETAILED DESCRIPTION OF CERTAIN EMBODIMENTS

Figure 1A:
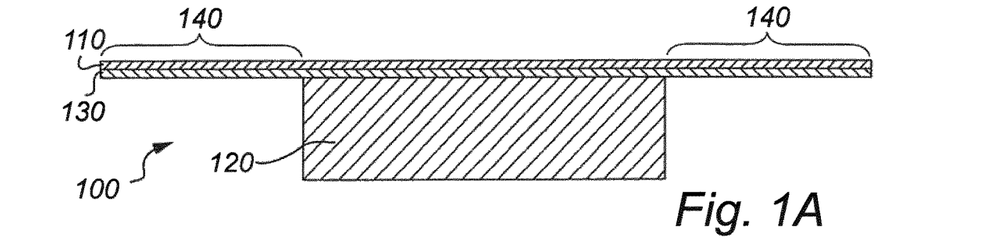

The present invention encompasses the discovery that border dressings detach from the patient during use at least partly because of air pockets that form at the edge of the wound pad and underneath the adhesive-coated border of such border dressings. The present inventor has discovered that these air pockets, areas where the adhesive-coated border has detached from the patient's skin, may expand during use and cause the wound dressing to detach such that the wound dressing no longer forms an air-tight seal around the wound. The inventor has found that in some cases, for example, in cases where dressings are used in a vertical position, wound exudates can accumulate in such air pockets. (See, for example, FIGS. 1C and 3C, showing the present inventor's proposed path of wound exudates, from the wound into the wound pad and, perhaps with the help of gravity, into an air pocket that is formed at the edge or contour of the wound pad.) Without wishing to be bound by any particular theory, such accumulation of wound exudates can wet the adhesive border portion of the wound dressing and/or create a pressure in the pocket, thus further contributing to detachment of the dressing.

The present inventor has further discovered that such air pockets form at least partly because border dressings do not typically lie flat against a patient's skin at the area around the edge of the wound pad.

According to embodiments of the present invention, an improved wound dressing is provided which eliminates or reduces formation of such air pockets. In some embodiments, such wound dressings exhibit prolonged adherence to a patient after application.

In one aspect, the present disclosure provides wound dressings generally comprising a backing layer, a wound pad, and a sealing ring. The wound pad has a wound-facing side and a non-wound-facing side and is affixed to the backing layer on its non-wound-facing side. As used herein, "wound-facing side" refers to the side of the dressing that, in use, faces the wound to which the dressing is applied, and "non-wound-facing side" refers to the side opposite of the wound-facing side. Before use, the wound facing side extends in a first geometrical plane, while the non-wound facing side extends in a second geometrical plane which is spaced from the first geometrical plane. In at least some embodiments, the sealing ring is pre-provided adhered to at least one other component in the wound dressing, e.g., a backing layer or an additional layer as described herein.

The wound pad has a circumferential contour. The circumferential contour can be regarded as the outer closed boundary of the wound pad located between the first and the second geometrical planes. At least a portion of the sealing ring is disposed between the first and the second geometrical planes and in the vicinity of the circumferential contour of the wound pad, such as within 5 mm and continuously along the contour of the wound pad. In contemplated embodiments of the invention, a portion of the sealing ring may extend beyond the first geometrical plane, for instance, be disposed on the wound-facing side of the dressing continuously along the entire contour of the wound pad. Therefore, the sealing ring may form a continuous, closed shape matching the shape of the wound pad. Examples of possible shapes include, but are not limited to, a triangle, a square, a rectangle, a circle, an ellipse, an oblong, and a heart shape.

Figure 2A:
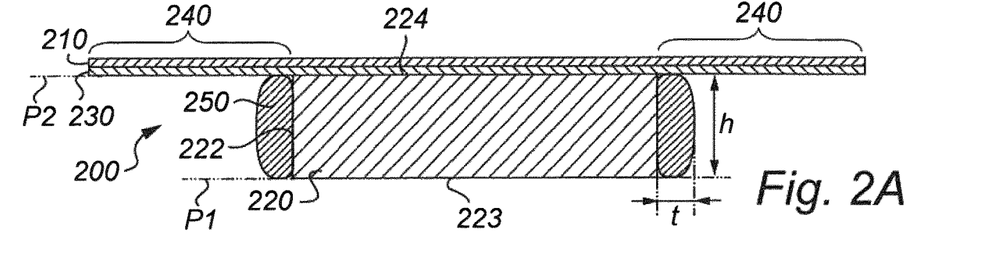
Figure 2B:
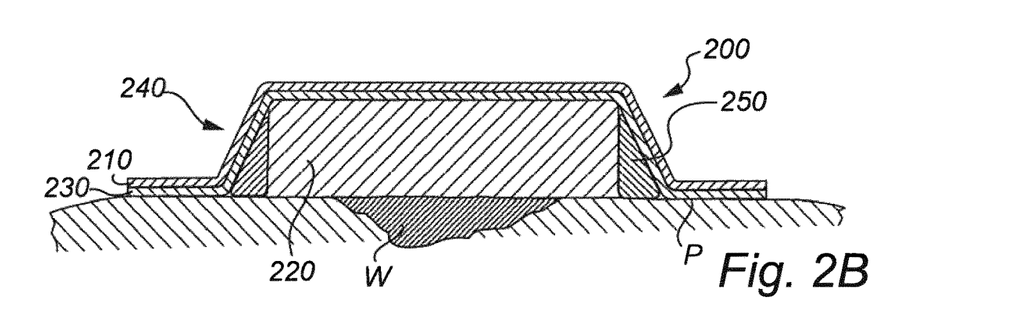
FIG. 2B depicts an exemplary wound dressing after it is applied to a wound.
Figure 2C:
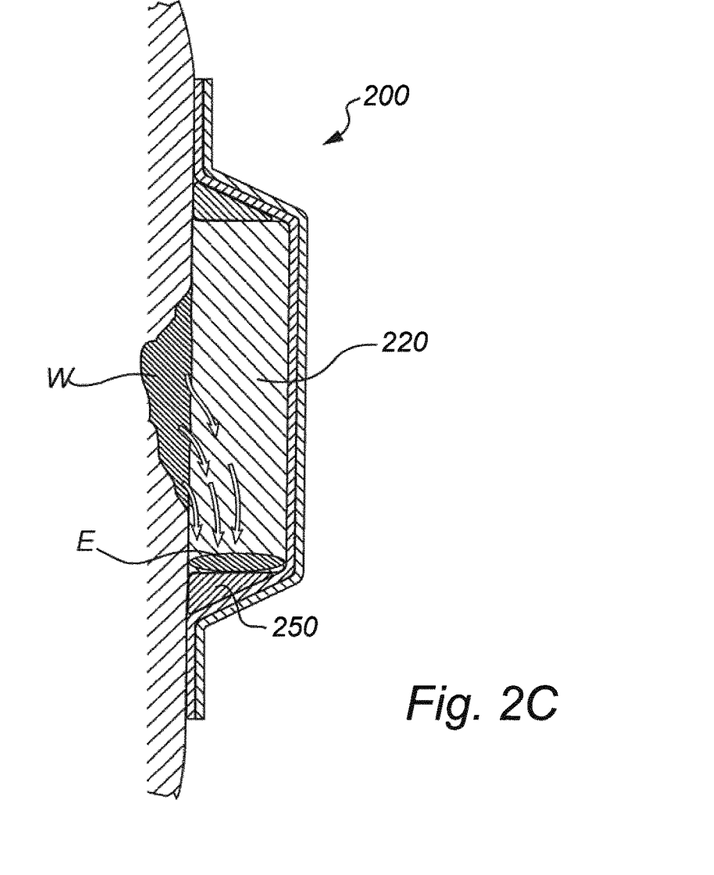
FIG. 2C shows the present disclosure's proposed mechanism for how wound exudates are retained in the wound pad.

Depending on the embodiment, the sealing ring is disposed directly on the backing layer or on an additional layer (such as, for example, a wound contact layer) as described herein. In embodiments in which there is no additional layer, at least a portion of the sealing ring is disposed on the backing layer, within 5 mm of and along the contour of the wound pad, throughout the entire contour of the wound pad. In some embodiments, at least a portion of the sealing ring is disposed within 4 mm of the contour of the wound pad throughout the entire contour of the wound pad. In some embodiments, at least a portion of the sealing ring is disposed within 3 mm of the contour of the wound pad throughout the entire contour of the wound pad. In some embodiments, at least a portion of the sealing ring is disposed within 2 mm of the contour of the wound pad throughout the entire contour of the wound pad. In some embodiments, at least a portion of the sealing ring is disposed within 1 mm of the contour of the wound pad throughout the entire contour of the wound pad. In some embodiments, the sealing ring is disposed immediately adjacent to the contour of the wound pad such that there is no gap (within manufacturing tolerances) between the contour of the wound pad and the sealing ring, throughout the entire contour of the wound pad. FIGS. 2A-C show, in cross section, an exemplary wound pad of some such embodiments.

Figure 4A:
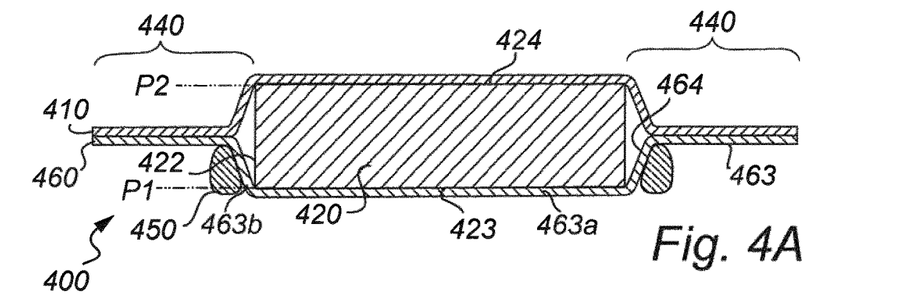
Figure 4B:
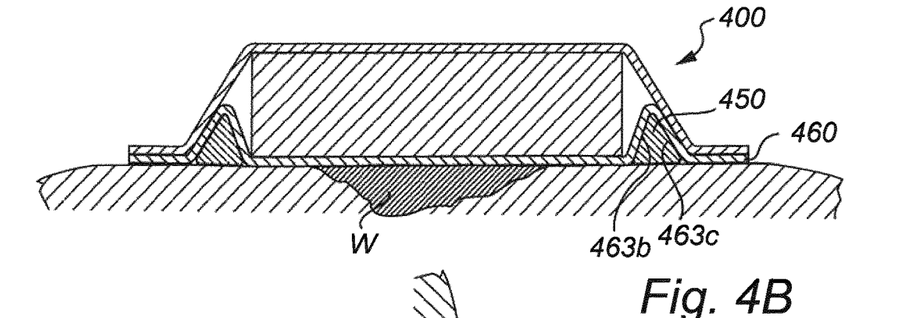
FIG. 4B depicts an exemplary wound dressing after it is applied to a wound.
Figure 4C:
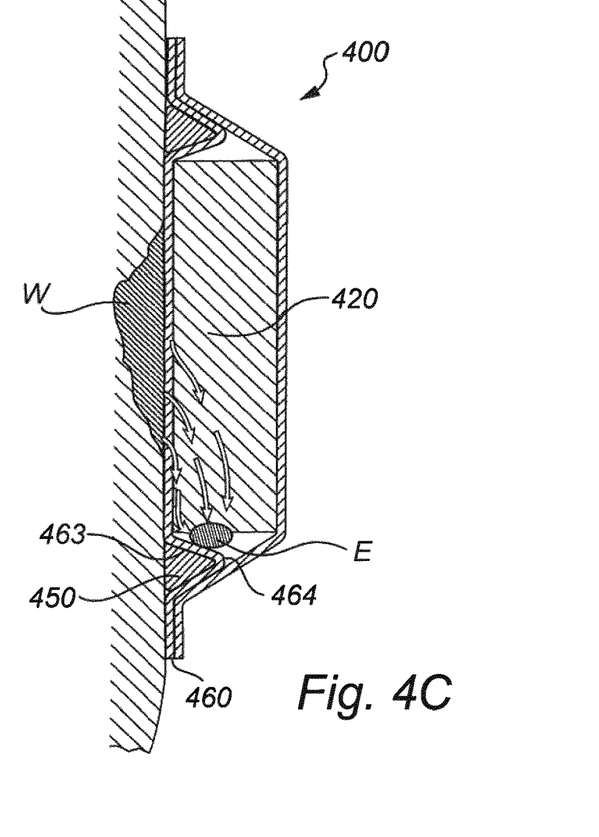
FIG. 4C shows the present disclosure's proposed mechanism for how wound exudates are retained in the wound pad.

In embodiments in which there is one or more additional layer(s) on the wound-facing side of the wound pad, at least a portion of the sealing ring is disposed on the additional layer that faces the wound when the dressing in use, within 5 mm, 4 mm, 3 mm, 2 mm, or 1 mm of the contour of the wound pad. In some such embodiments, the sealing ring is disposed almost immediately adjacent to the wound pad, except that the one or more additional layer(s) on the wound-facing side of the wound pad separates the sealing ring from the wound pad. FIGS. 4A-C show, in cross section, such an exemplary wound pad. In the embodiment shown in FIGS. 4A-C, there is only a minute gap between the wound pad and the sealing ring in the horizontal (with respect to FIG. 4A-C) direction, and the gap is entirely filled by a wound contact layer.

In use, the sealing ring lies adjacent to the wound site (e.g., the patient's skin and/or wound).

Whether or not an additional layer is included, in at least some embodiments, no part of the sealing ring is disposed beneath (i.e., on the wound-facing side of) the wound pad before the wound dressing is applied to the patient. Thus, when in use, either no or only a very small part of the sealing ring is disposed between the wound pad and the wound site or patient's skin to which the wound dressing is applied.

In some embodiments, when the dressing is applied, the sealing ring fills at least partly a space adjacent to the wound pad. (See, for example, FIGS. 2B, 2C, 4B, and 4C.) In some embodiments, the sealing ring substantially fills the space adjacent to the wound pad and between a border portion of the wound dressing (e.g. including the backing layer and/or other additional layer, e.g. wound contact layer) and the wound and/or patient's skin during use. Without wishing to be bound by theory, it is proposed that, in a comparable wound dressing without a sealing ring, such a space would remain unfilled and may form an air pocket, which may expand during use and contribute to detachment of the wound dressing.

In general, the sealing ring comprises or is comprised of a soft, elastic (and suitably skin adherent) material that can provide a fluid seal when the dressing is in use. In some embodiments, the sealing ring comprises or is comprised of a hydrophobic material. Examples of suitable materials include, but are not limited to, polymer gels or elastomers, hydrocolloids, hydrogels, and natural gums (e.g., xanthan, guar, cellulose). Examples of suitable polymer gels include, but are not limited to, silicone polymer gels, polyurethane polymer gels, polyolefin-based gel polymers, and acrylic gels.

In some embodiments, the sealing ring is comprised of a silicone gel, e.g., a silicone elastomer. A variety of silicone elastomers suitable for use in medical devices are commercially available, such as, for example, chemically cross-linked silicone gels such as polydimethyl siloxane gels. As an example, platinum-catalyzed two-component room-temperature vulcanizing (RTV) systems, for example, in which vinyl-substituted polydimethylsiloxane and hydrogen-substituted polydimethylsiloxane is crosslinked by a hydrosilylation reaction, can be used. For example, the sealing ring may comprise a soft silicone gel having as softness (penetration) of from 8 to 22 mm, such as for example from 12 to 17 mm, as measured by a method based on ASTM D 937 and DIN 51580, further disclosed below. One example of a commercially available RTV addition-cured silicone systems is Wacker SilGel 612 which is a two-component system, wherein the softness and degree of adherence of the formed elastomer (or gel) can be varied by varying the proportions of the two components A:B from 1.0:0.7 to 1.0:1.3. Other examples of suitable soft silicone gels include: the Q72218 silicone gel system from Dow Corning (Midland, Mich., United States), NuSil MED-6340, NuSil MED3-6300, NuSil MED12-6300 from NuSil Technology (Carpinteria, Calif., United States).

In some embodiments, the sealing ring is comprised of a biocompatible material. In some embodiments, the sealing ring is comprised of a material that is compliant with regulatory standards for safety of medical devices, e.g., Food and Drug Administration standards. For example, in some embodiments, the sealing ring is comprised of a material that is free of one or more of organic plasticizers (such as bisphenol A), phthalates, and latex additives. For example, the sealing ring may be comprised of a material that is free of all of: organic plasticizers, phthalates, and latex additives.

Although the sealing ring has been described in some embodiments as being hydrophobic, in other embodiments, the sealing ring may comprise an absorbent material as long as it performs the described function of limiting or preventing exudates to flow to the peripheral areas of the wound dressing.

In some embodiments, the sealing ring adheres to human skin.

In some embodiments, each part of the sealing ring has a cross section (which is perpendicular to the first and second geometrical planes and which can be viewed in a cross section of the wound dressing, as shown, for example, in FIGS. 2 and 4). In some embodiments, the cross section has a substantially constant shape and size throughout the sealing ring. The shape of this cross section may be, for example, circular, oval, elliptical, square, rectangle, triangular, etc. The original shape of the cross section of the sealing ring, i.e. before use, may become deformed when the wound dressing is applied to the patient's skin.

The dimensions of the cross section of the sealing ring are generally chosen such that when the wound dressing is in use, the sealing ring can conform to and fill the space adjacent to the wound pad and between the wound dressing and the wound site. Accordingly, the dimensions of the cross section of the sealing ring may depend at least partly on one or more of: the thickness of the wound pad, the compressibility or conformability of the material comprising the sealing ring, and the compressibility or conformability of the wound pad. For example, in some embodiments, the wound pad is comprised of a compressible polyurethane foam having a thickness of about 5 mm, and the sealing ring is comprised of a silicone elastomer with an approximate triangular and constant cross section throughout, the cross section having sides about 2-5 mm in length.

The sealing ring may be adhered to a layer of the wound dressing, e.g., to the backing layer and/or to a wound contact layer (if present) by any of several methods known in the art. For example, the sealing ring may be adhered by being disposed onto the layer to which it should be adhered in an uncured or partially uncured state, and then allowed to cure or finish curing. Alternatively or additionally, the sealing ring may be adhered to a layer of the wound dressing using an adhesive, such as any of the aforementioned materials of which the sealing ring may be comprised.

In some embodiments, the sealing ring is formed by extruding or otherwise depositing material from which it is made onto the layer of the wound dressing to which it will be adhered, either directly or with the use of an adhesive. In some embodiments, the sealing ring is formed in the desired shape and size on a separate surface and then transferred to the layer on the wound dressing to which it will be adhered, either directly or with the use of an adhesive.

In some embodiments, the sealing ring is extruded by a nozzle or a syringe.

In some embodiments, the sealing ring, after application to a wound site, adheres at least partly to the wound site without the application of additional components. Generally, the adhesion between the sealing ring and the layer to which it is bonded is stronger than any adhesion between the sealing ring and the wound site, so that, when removal of the wound dressing is desired, the wound dressing can be removed from the wound site without any component of the wound dressing being dislodged from the other components.

The backing layer is typically a thin film, sheet, or membrane that is vapour permeable and waterproof. Examples of suitable materials for the backing layer include, but are not limited to, polyurethane films, silicone films, polyester-based nonwoven mterials, and laminates of polyester-based nonwoven materials and polyurethane films The backing layer is typically bonded to the wound pad, for example, via an adhesive such as a pressure sensitive adhesive (such as an acrylic adhesive). If an additional layer such as a wound contact layer is included, the backing layer is typically also bonded to the additional layer in those parts of backing layer that extend beyond the wound pad.

In some embodiments, provided wound dressings further comprise one or more additional layers. For example, in some embodiments, a wound contact layer is provided on the wound-facing side of the wound pad and extends peripherally beyond the edges of the wound pad. In some embodiments, the wound contact layer is co-extensive with the backing layer in that both layers have the same outer dimensions, and is bonded to the backing layer in those areas of both layers that extend beyond the periphery of the wound pad.

In some embodiments, the wound contact layer is perforated. In some embodiments, perforations in the wound contact layer form a regular pattern.

The wound contact layer can be comprised of any of a variety of materials known in the art and suitable for use in a medical device. In some embodiments, the wound contact layer is comprised of a thin plastic film, or a laminate comprising a thin plastic film, coated with an adhesive as described further below. Suitable materials for the thin plastic film include, but are not limited to, polyolefin-based fillms (such as, e.g., polyethylene), polyamide, polyurethane, and silicone. In some embodiments, the wound contact layer is comprised of a thin polyurethane film.

As used herein in reference to a wound dressing of the present disclosure, the term "border" refers to that portion of the wound dressing that extends beyond the periphery of the wound pad. The border generally comprises a portion of the backing layer. In some embodiments, the border also comprises a portion of one or more additional layers, for example, a wound contact layer disposed on the wound-facing side of the wound pad and on the wound-facing side of the border portion of the backing layer. In some embodiments, the backing layer extends beyond the periphery of the sealing ring, although in other embodiments another layer (which may e.g. be suitably connected to the backing layer) extends beyond the periphery of the sealing ring. Thus, in a general sense, in some embodiments the border extends over the sealing ring and beyond the periphery of the sealing ring. The sealing ring limits or prevents exudates from reaching the peripheral areas of the border. In some embodiments of the invention, at least the surface of the border that is intended to lie adjacent to the wound site (e.g., on a patient's skin or wound) during use is coated with an adhesive. However, in other embodiments the wound dressing is produced without an adhesive border for attachment to a patient's skin, in which case an adhesive may be added to the wound dressing before applying the wound dressing on the wound. Other means, such as tapes, for attaching the wound dressing to a patient's skin are conceivable. In some embodiments, additional areas of the surface intended to lie adjacent to the wound site are also coated with an adhesive—for example, the non-border portion of the wound dressing.

In some embodiments, the adhesive is comprised of a hydrophobic material.

Examples of suitable adhesives include, but are not limited to, silicone gels, hot melt adhesives, acrylate adhesives, polyurethane gels, and hydrocolloid adhesives. In some embodiments, the adhesive is comprised of a material that is non-irritating to skin, for example, a silicone gel. Examples of suitable silicone gels include the two-component RTV systems such as Q72218 (Dow Corning) and SilGel 612 (Wacker Chemie AG) mentioned herein, as well as the NuSil silicone elastomers. In embodiments of the invention, the adhesive may comprise a silicone gel. For example, the adhesive may comprise a soft silicone gel having as softness (penetration) of from 8 to 22 mm, such as for example from 12 to 17 mm, as measured by a method based on ASTM D 937 and DIN 51580, further disclosed below.

Wound pads generally comprise an absorbent, conformable material such as, for example, foams and/or cellulose-based materials (such as, e.g., a hydrocellulose). The wound pad may comprise a hydrophilic material, e.g., a hydrophilic foam. Suitable foam materials include, but are not limited to polyurethane foams. In some embodiments, the wound pad comprises a porous foam.

In some embodiments, the wound pad is a multilayered wound pad. For example, the wound pad may comprise two or more layers having different properties laminated together. Suitable multilayered wound pads include, but are not limited to, those described in International Patent Application WO2010/147533A1, the entire contents of which are incorporated herein by reference. For example, the wound pad can comprise a first absorbent layer on its wound-facing side and a second absorbent layer on its non wound-facing side, with the second absorbent layer being affixed to the backing layer. In some such embodiments, another layer is disposed between the first absorbent layer and the second absorbent layer, for example, a liquid distributing layer, which can act to spread liquid absorbed by the first absorbent layer and transmit the liquid to the second absorbent layer.

In some embodiments, the first absorbent layer is comprised of a foam, for example, a hydrophilic foam such as a hydrophilic polyurethane foam.

In some embodiments, the second absorbent layer comprises super-absorbent fibers. For example, polyacrylic super-absorbent fibers may be suitable. The second absorbent layer may also comprise binding fibers, non-limiting examples of which include polyester fibers, polyethylene fibers, polypropylene fibers, and blends thereof. Alternatively or additionally, the second absorbent layer may comprise cotton fibers.

In some embodiments, the liquid distributing layer is thinner than both the first and second absorbent layers. In some embodiments, the liquid distributing layer is comprised of a nonwoven material, such as, for example, viscose, polyester, or both.

In some embodiments, provided wound dressings further comprise a release layer, intended to be removed before use. If no wound contact layer is present, the release layer is disposed on and releasably attached to the wound-facing side of the wound pad and the border portion of the backing layer. If a wound contact layer is present, the release layer is disposed on and releasably attached to the wound-facing side of the wound-contact layer. By "releasably attached," it is meant that the release layer may be peeled away from the rest of the wound dressing by hand. The release layer acts as a barrier that can protect the sterility of the wound pad and any adhesive present on the wound-facing surface of the backing layer, wound pad, and/or wound contact layer before the dressing is not used. The release layer may be releasably attached to the rest of the wound dressing via any such adhesive present. The release layer may be made of any of a variety of suitable materials known in the art, such as, for example, polyethylene, polyester, polypropylene, an silicone-coated paper.

In some embodiments, provided wound dressings comprise a port in the backing layer that allows fluid communication between the wound dressing connection and a conduit connected to the port, e.g., for use in a negative pressure wound treatment system, as further described below. In some such embodiments, the port extends into the wound pad and allows fluid communication between the wound pad and a conduit connected to the port.

Negative Pressure Wound Treatment Systems

Another aspect of the present disclosure is directed to systems for negative pressure wound treatment that comprise a negative pressure source for providing negative pressure to a wound, a conduit configured to transmit negative pressure from the negative pressure source to the wound, and a wound dressing of the present disclosure as described herein.

In use, the wound dressing is disposed over the wound and affixed to the wound site. Generally, the wound dressing is attached to the skin surrounding the wound, and, either alone or in combination with one or more other components of the negative pressure system, forms an airtight seal over the wound.

The conduit is fluidly coupled at one end (hereinafter the "proximal end") to the wound and at one end (hereinafter the "distal end") to the negative pressure source. In some embodiments, the proximal end of the conduit is integrated into the wound dressing, e.g., via a hole or a port. The hole or port may be sealed in an airtight manner, that is, such that air does not leak from the interior of the conduit to the environment and vice versa.

In some embodiments, the system further comprises a storage canister in fluid communication with the conduit for collecting fluid such as wound exudate. In embodiments comprising a storage container, a filter may be included to prevent fluids, aerosols, and/or other contaminants from leaving the container.

Figure 7:
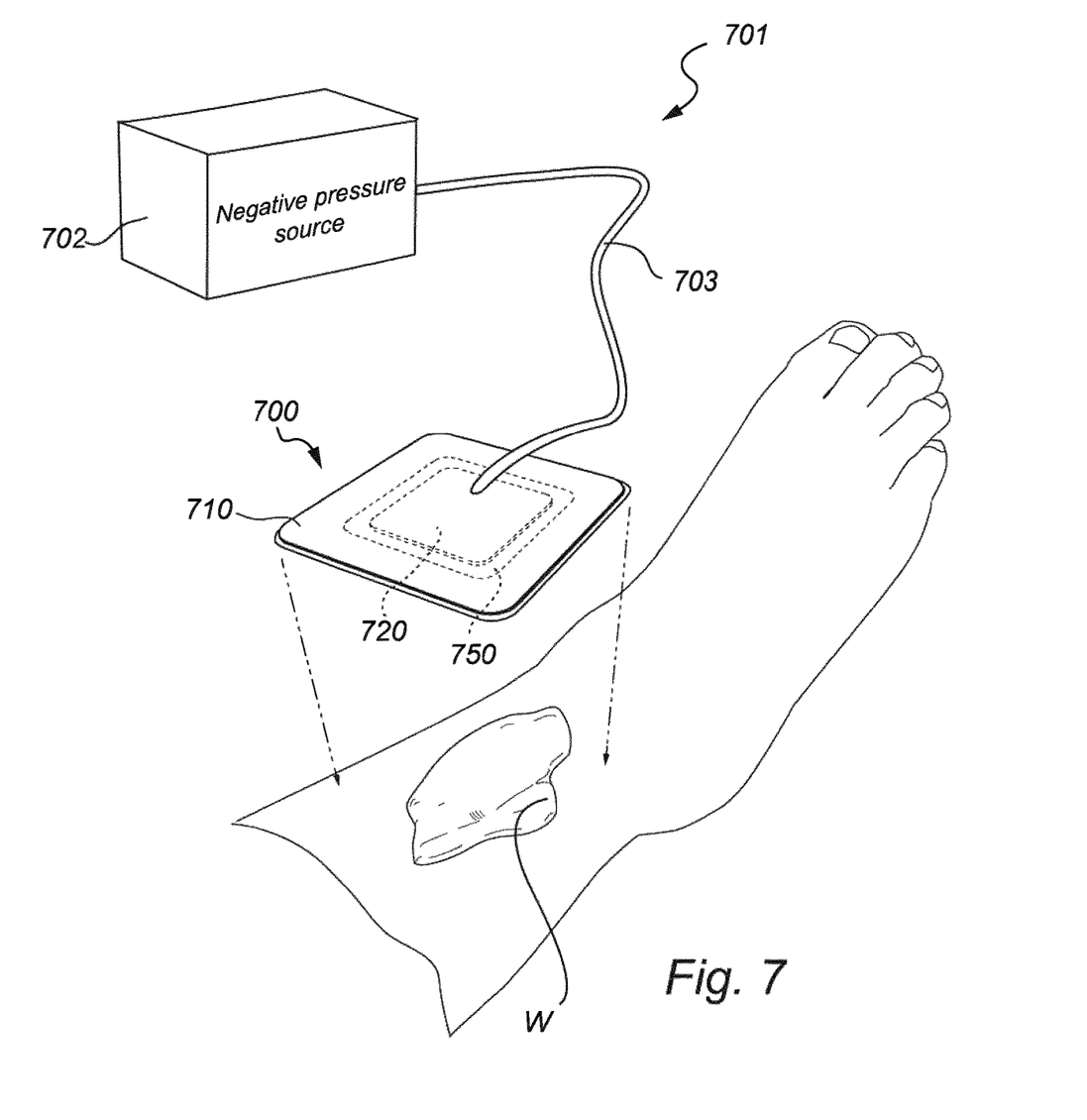
FIG. 7 depicts an exemplary negative pressure wound treatment system of the present disclosure.

An exemplary embodiment of a system for negative pressure wound treatment is illustrated in FIG. 7. The system comprises a negative pressure source for providing negative pressure to a wound, a conduit, and a wound dressing of the present disclosure as described herein. The conduit is configured to transmit negative pressure from the negative pressure source to the wound via the wound dressing. In FIG. 7, the illustrated conduit is a single-lumen conduit. However, other conduit configurations may be used, as described below.

The negative pressure source may comprise a pump, non-limiting examples of which include vacuum pumps (e.g., electrically-driven vacuum pumps, manually actuated pumps, piezoelectric-actuated pumps, etc.), circulation pumps, dual action vacuum/pressure pumps (e.g. for drainage and irrigation), peristaltic pumps, syringe pumps, bellows pumps, diaphragm pumps, and combinations thereof. Pumps in systems of the present disclosure are generally adapted to provide a negative pressure value that is suitable for treatment protocols standard in the art. In some embodiments, the negative pressure source includes one or more pressure sensors for detecting a pressure within the system. In some embodiments, the pump is a miniature pump located on top of the wound dressing, or integrated within the wound dressing.

Depending on the embodiment, the negative pressure source may be adapted to provide negative pressure at a fixed negative pressure value or may be adapted to provide negative pressure at one of multiple values which may be selected, for example, by the user and/or depending on the therapy mode. In some embodiments, the negative pressure source is adapted to provide negative pressure at various values within a range. In some such embodiments, the negative pressure source is adapted to provide negative pressure at any value in certain increments from a lower limit (absolute value) to an upper limit (absolute value).

The negative pressure source may be adapted to provide negative pressure continuously during treatment. Alternative or additionally, the negative pressure source is adapted to provide negative pressure intermittently during treatment.

Generally, the negative pressure source is adapted to provide negative pressure at one or more values that fall within the range between about 20 mm Hg and about 400 mm Hg (inclusive of endpoints; values herein refer to the absolute values of negative pressure unless otherwise indicated).

It is contemplated that the threshold values used during negative pressure wound therapy may include, for example, any value in the range between about 20 mm Hg and about 400 mm Hg (inclusive of both endpoints), for example, about 20 mm Hg, about 25 mm Hg, about 50 mm Hg, about 60 mm Hg, about 80 mm Hg, about 120 mm Hg, about 200 mm Hg, or about 300 mm Hg. For example, in some embodiments, a negative pressure of about 80 mm Hg is used. In some embodiments, a negative pressure of about 120 mm Hg is used. In some embodiments, a negative pressure of about 80 mm Hg is used. In some embodiments, a negative pressure of about 40 mm Hg is used.

The selection of the appropriate values may be made, for example, by a clinician or patient. The choice of appropriate negative pressure value(s) may be influenced by any or a combination of factors such as location of wound, type of wound, wound healing status, type and/or material of wound pad, type of dressing, patient, etc. In some embodiments where the wound pad is comprised of a polymer foam, a negative pressure of about 120 mmHg is used.

In some embodiments, the negative pressure source may be adapted to provide a negative pressure, the absolute value of which is greater than or equal to about 120 mmHg or about 180 mmHg.

In some embodiments, the conduit is provided via a single lumen tube. In some embodiments, the conduit is provided as part or all of a multi-lumen tube, for example, wherein one lumen is used to provide negative pressure to the wound, and one or more additional lumens may be used for another purpose, e.g., circulation, measurement (e.g. of pressure), irrigation, etc.. In embodiments with multiple lumens, any of a variety of possible arrangements of the lumens is possible, e.g., parallel lumen arrangements, central and peripheral lumen arrangements, etc.

In some embodiments, such as in embodiments in which the pump is disposed on or within the wound dressing, the conduit is provided via one or more channels.

In some embodiments, fluid is transported via the conduit. For example, wound exudates may be transported away from the wound via the conduit. In embodiments with a canister, wound exudates may be transported into the canister.

DETAILED DESCRIPTION OF THE DRAWINGS

FIG. 1 depicts cross sections of a prior art wound dressing 100.

The prior art wound dressing 100 is shown before it is applied to a wound in FIG. 1A. The wound dressing 100 comprises a backing layer 110 and a wound pad 120 attached to the backing layer 110 via an adhesive layer 130. The areas of the backing layer 110 and adhesive layer 130 which extend beyond the periphery of the wound pad are referred to as the border 140 of the wound dressing 100.

Figure 1B:
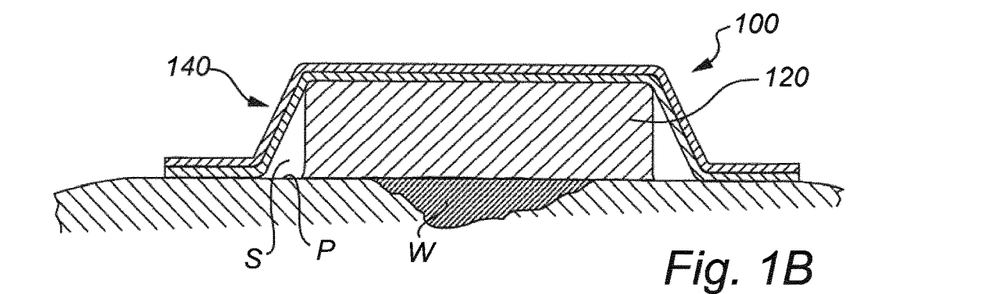
FIG. 1B depicts the present disclosure's proposed sketch of the wound dressing after it is applied to a wound.
Figure 1C:
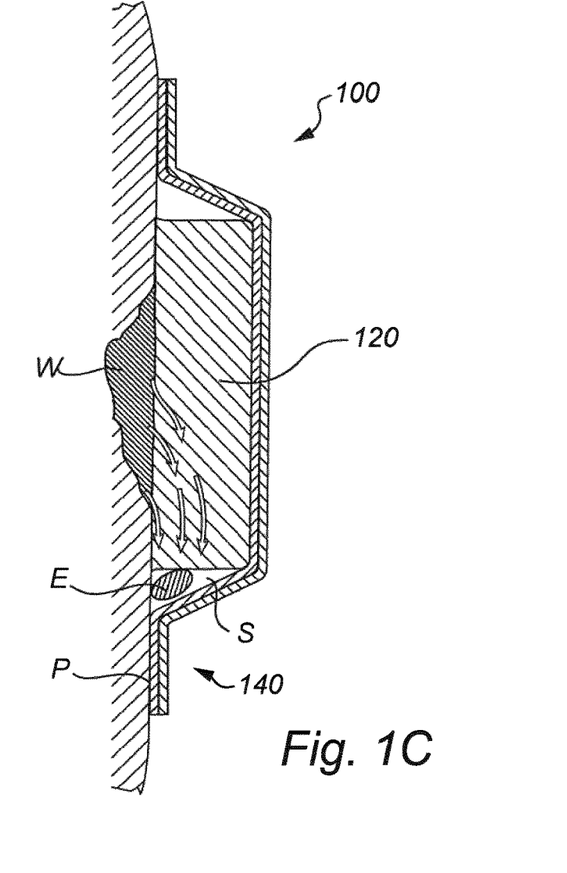
FIG. 1C shows the present disclosure's proposed mechanism for how wound exudates can accumulate in the space adjacent to the wound pad of such a prior art wound dressing.

FIG. 1B depicts the present disclosure's proposed sketch of the wound dressing 100 after it is applied to a wound W. Around the periphery of the wound pad 120, an annular space S in the form of an air pocket is formed between the border 140 and the skin P of the patient.

FIG. 1C shows the present disclosure's proposed mechanism for how wound exudates E can accumulate in the space S adjacent to the wound pad 120 of such a prior art wound dressing 100. The wound dressing 100 is illustrated in a vertical position, for instance on a leg of a person standing. It is believed that the gravitational force causes the exudates E to leak from the wound pad 120 and into the space S. This may cause at least partial loosening of the border 140 from the skin P, leaking of exudates from the wound dressing, and possibly entry of non-desired substances or bacteria into the wound. Furthermore, exudates on the surrounding skin P may cause maceration.

FIG. 2 depicts cross sections of exemplary wound dressings 200 of the present disclosure.

An exemplary wound dressing 200 is shown before it is applied to a wound in FIG. 2A. The wound dressing 200 has a backing layer 210 and a wound pad 220. In this exemplary embodiment the wound pad 220 is attached to the backing layer 210 via an intermediate adhesive layer 230. However, in other embodiments, adhesive does not need to be provided on the wound pad 220, but only on the border 240, or a part of the border. For instance, it may be enough to provide adhesive at the peripheral edge portions of a wound facing side of the backing layer 210 for enabling adhering of the wound dressing 200 to the skin of a patient. The border 240 is the part of the backing layer 210 (and any additional layer such as the adhesive layer 230) which extends beyond the periphery (circumference) and contour 222 of the wound pad 220.

The wound pad has a wound-facing side 223 extending in a first geometrical plane P1 and a non-wound facing side 224 extending in a second geometrical plane P2. Thus, in the illustrated and other exemplary embodiments, the wound pad 220 is, via the adhesive layer 230, affixed to the backing layer 210 on the wound pad's non-wound facing side 224. Generally, the geometrical planes P1 and P2 are parallel to each other. The thickness or height of the wound pad may thus correspond to the separating distance between the geometrical planes P1 and P2.

The wound pad 220 has a circumferential contour 222 which defines the peripheral boundaries of the wound pad 220 between the first and the second geometrical planes P1 and P2. A sealing ring 250 is disposed annularly around the wound pad 220. In the illustrated and other exemplary embodiments the sealing ring 250 is attached to the backing layer 210 via the adhesive layer 230. In other embodiments, the sealing ring 250 may be in direct contact with the backing layer 210. Thus, in general terms, in at least some exemplary embodiments, a cross-section of the sealing ring 250 extends from the second geometrical plane P2 in a direction towards the first geometrical plane P1. The length of extension in the direction from one of the geometrical planes to the other defines a height h of the sealing ring 250. A thickness t of the sealing ring 250 is regarded as being perpendicular to the height h and extending in a direction away from the wound pad 220. Different embodiments may have different heights h and/or thicknesses t. For example, in embodiments of the invention, the height h of the sealing ring may substantially be the same as, or larger than, the distance between the first and the second geometrical planes, that is, the height h may substantially correspond to the thickness of the wound pad. Accordingly, the sealing ring may cover the entire circumferential area (or thickness) of the wound pad. A large height of the sealing ring increases the sealing effect of the sealing ring. Although the sealing ring may already provide some initial contact with the skin when the wound dressing is initially just placed over the wound (the configuration will be similar to what is shown in FIG. 2A), the contact will be higher for the long-term use, as some of the height of the sealing ring will be compressed to locally increase the thickness of the sealing ring so as to increase the contact between the sealing ring and the skin P of the patient (see FIGS. 2B and 2C). Furthermore, as shown in FIGS. 2B and 2C, the resulting triangular cross-section in this case (other shapes are however also conceivable) will still retain a blocking function closer to the second geometrical plane P2. However, although the entire wound pad 220 may absorb exudates, the wound facing side 223 of the wound pad 220 is the one that is most exposed to the exudates, and therefore the thickness of the sealing ring 250 in the functional state (FIGS. 2B and 2C) of the wound dressing is largest at the skin interface, i.e. at the base of the triangle.

In at least some exemplary embodiments, which also include embodiments having wound contact layers such as in FIG. 4, a cross-section of the sealing ring extends from the border (be it a backing layer with or without an adhesive layer, or including a wound contact layer) in a direction towards the first geometrical plane P1. In some exemplary embodiments, the cross-section of the sealing ring extends all the way to the first geometrical plane P1 or even beyond the first geometrical plane P1 (i.e. the height h may be substantially equal to or greater than the separating distance between the planes P1 and P2). As previously explained, a large height provides an advantageous sealing effect. In other exemplary embodiments, a cross-section of the sealing ring starts from a location between the geometrical planes P1 and P2 and extends in a direction towards the geometrical plane P1.

In the illustrated and other exemplary embodiments the sealing ring 250 is in direct contact with the wound pad 220. In other exemplary embodiments the sealing ring may, before use, be separated from the wound pad at a distance of no more than 5 mm.

In at least some exemplary embodiments, such as the one illustrated in FIG. 2A, before use of the wound dressing 200, the height h of the sealing ring is larger than the thickness t of the sealing ring. For instance, the thickness t may be less than 70% of the height h, such as 10-50%, for instance 20-40%.

FIG. 2B depicts the exemplary wound dressing 200 after it is applied to a wound W. The wound pad 220 covers the wound W, while part of the adhesive layer 230 adheres the wound dressing 200 to surrounding skin area P. As can be seen in the illustration, the sealing ring 250 has become deformed. The cross-section of the sealing ring 250 may, for instance, become substantially triangular, herein illustrated as a substantially right triangle. Also, the border 240 extends at a non-perpendicular angle from the first plane P1 to the second plane P2, here illustrated as substantially following the hypotenuse of the right triangle. The sealing ring 250 has become sandwiched or enclosed between the border 240 and the wound pad 220.

FIG. 2C shows the present disclosure's proposed mechanism for how wound exudates E are retained in the wound pad 220. FIG. 2C illustrates a part of the body in a vertical position, for instance a part of a leg of a person standing. Even though exudates E, which have entered the wound pad 220 may be driven downwards by gravity, as illustrated by the arrows, they are prevented from leaking past the sealing ring 250. Hereby, the problems of the prior art may be avoided.

An advantage of having a smaller thickness t than the height h as illustrated in FIG. 2A is that in the applied state (FIGS. 2B and 2C) the border is allowed to approach skin P at steep inclination. This in turn means that the effective contact area between the border 240 and the skin P is not compromised (compared to the prior art in FIGS. 1B and 1C), while obtaining the advantage of a large contact area between the sealing ring 250 and the skin P.

Figures 3A, 3B:
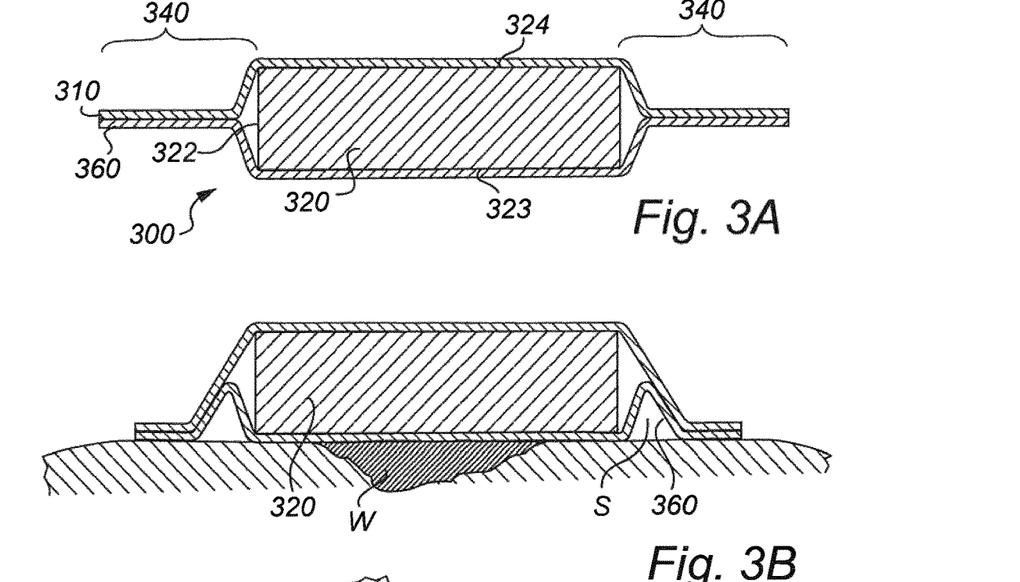
Figure 3C:
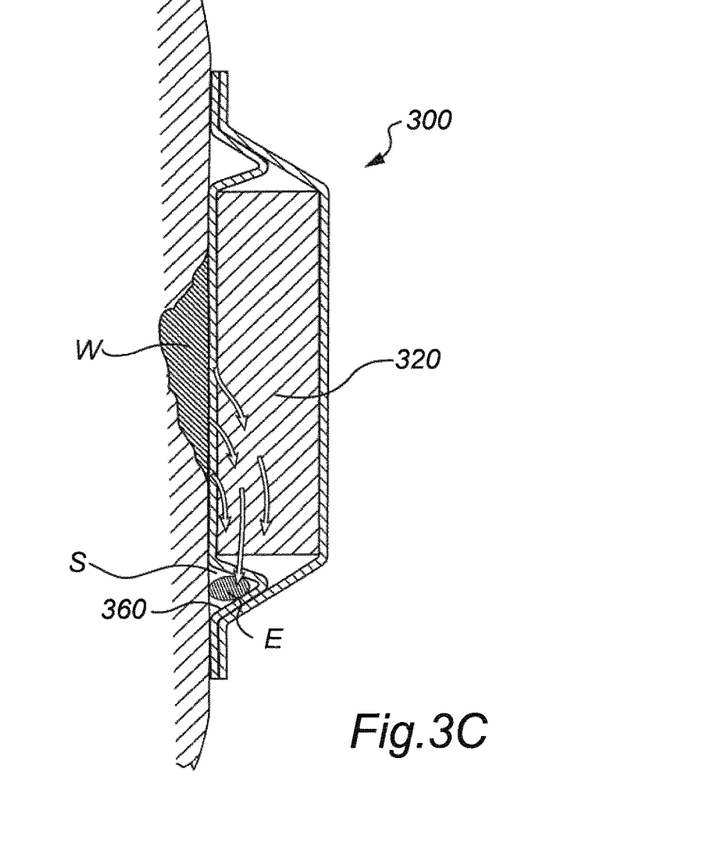
FIG. 3C shows the present disclosure's proposed mechanism for how wound exudates can accumulate in the space adjacent to the wound pad of such a prior art wound dressing.

FIG. 3 depicts cross sections of a prior art wound dressing 300 having a wound contact layer 360. The prior art wound dressing 300 is shown before it is applied to a wound in FIG. 3A. The part of the backing layer 310 and wound contact layer 360 extending beyond the periphery 322 of the wound pad 320 is referred to as the border 340. As can be seen in FIG. 3A the backing layer 310 extends from the non-wound facing side 324 of the wound pad 320, while the wound contact layer 360 extends from the wound-facing side 323 of the wound pad 320, and they meet each other at a geometrical plane which is located between the wound-facing side 323 and the non-wound facing side 324 of the wound pad 320.

The wound contact layer 360 may comprise or be provided with adhesive for facilitating adhering to the skin. FIG. 3B depicts the present disclosure's proposed sketch of the wound dressing 300 after it is applied to a wound W. In the applied position, the wound contact layer 360 tends to define an annular space S around the wound pad 320.

FIG. 3C shows the present disclosure's proposed mechanism for how wound exudates E can accumulate in the annular space S adjacent to the wound pad 320 of such a prior art wound dressing 300. The wound contact layer 360 is liquid permeable in both directions. Thus, first it allows exudates E to pass from the wound W through the wound contact layer 360 from one side into the wound pad 320, and then as exudates driven by gravity leave the wound pad 320 the exudates pass from the other side of the wound contact layer 360 and accumulate in said space S, potentially leading to the previously described drawbacks, such as maceration of surrounding skin areas.

FIG. 4 depicts cross sections of exemplary wound dressings 400 of the present disclosure having wound contact layers 460. An exemplary wound dressing 400 is shown before it is applied to a wound in FIG. 4A. A backing layer 410 is arranged on a non-wound facing side 424 of the wound pad 420, substantially in the geometrical plane P2. A liquid permeable wound contact layer 460 extends on the wound-facing side 423 of the wound pad 420, substantially in the geometrical plane P1. The border 440 of the wound dressing 400, i.e. the part of the backing layer 410 and the wound contact layer 460 extending beyond the circumferential contour 422 of the wound pad 420, is located between the geometrical planes P1 and P2. In the illustrated embodiment, the wound contact layer 460 meets the backing layer 410 substantially halfway between the geometrical planes P1 and P2, however, in other embodiments they may meet closer to one of the planes P1 and P2. In some embodiments, the height of the sealing ring substantially corresponds to half the thickness of the wound pad.

The wound contact layer 460 has a wound-facing side 463 and a non-wound facing side 464. It should be noted that only a portion of the wound-facing side 463 of the wound contact layer 460 is actually intended to face the wound, namely a portion 463a of wound-facing side 463 of the wound contact layer 460 which is in contact with the wound pad 420. The peripheral portions (forming part of the border 440) of the wound-facing side 463 of the wound contact layer 460 are intended to be applied to, and thus face, skin areas surrounding the wound.

Similarly to FIG. 2, in FIG. 4 a sealing ring 450 is attached to the border of the wound dressing. As can be seed in FIG. 4A, the sealing ring 450 is attached to the wound-facing side 463 of the wound contact layer 460. In at least the illustrated embodiment, the sealing ring 450 is located at a portion 463b of the wound contact layer 460 which is substantially free from contact with the wound pad 420 and the backing layer 410. This free portion 463b is illustrated in the cross-sectional view as extending obliquely from the first plane P1 towards the backing layer 410.

The thickness of a cross-section of the sealing ring 450 may be equal to or smaller than a height of the cross-section, for instance, the thickness may be 30-100% of the height, such as 40-90%, for example, 50-80%. Although the relative height compared to the thickness of the sealing ring 450 is smaller than in the embodiment of FIG. 2A, the present sealing ring 450 also provides for a good sealing effect. The height of the sealing ring 450 may suitably correspond to half the thickness of the wound pad 420. The cross-sectional geometry of the sealing ring may be designed in such way that compared to the prior art shown in FIGS. 3B and 3C, the contact area between the skin and the wound contact layer 460 will not be compromised while providing the advantage of a large contact area between the sealing ring 450 and the skin, as can be seen in FIGS. 4B and 4C.

FIG. 4B depicts an exemplary wound dressing 400 after it is applied to a wound W. As can be seen the free portion 463b of the wound contact layer 460 forms together with a portion 463c of the wound contact layer 460 attached to the backing layer 410 an annular confined space which (together with the skin) defines and/or limits the deformation of the sealing ring 450. In at least the illustrated example, the cross section of the annular confined space is substantially triangular, as is the cross-section of the deformed sealing ring 450. N.B. in the illustrated drawing the sealing ring 450 takes up the entire confined annular space (therefore no separate reference numeral/letter is given to the confined annular space).

FIG. 4C shows the present disclosure's proposed mechanism for how wound exudates E are retained in the wound pad 420. Thus, even though the wound contact layer 460 is liquid permeable, exudates E are prevented from leaking past the sealing ring 450, and will be kept substantially in the wound pad 420 and in a space on the non-wound facing side 464 of the wound contact layer 460. By reducing the amount of exudates E that pass from the wound pad 420 to the wound-facing side 463 of the wound contact layer 460, the risk of the wound contact layer 460 loosening from the skin is reduced.

Figure 5:
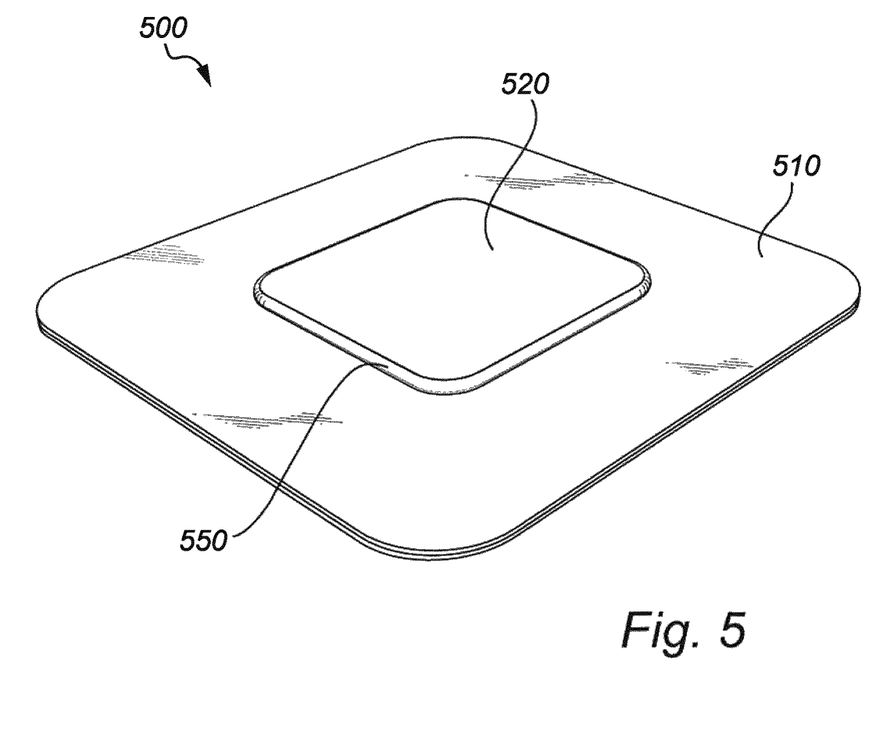
FIG. 5 depicts a top view of a wound dressing of the present disclosure, showing the position of the sealing ring relative to the wound pad.

FIG. 5 depicts a top view of a wound dressing 500 of the present disclosure, showing the position of the sealing ring 550 relative to the wound pad 520. For instance, it could be a wound dressing of the type shown in FIG. 2. In FIG. 5, the wound dressing 500 is illustrated as having a substantially square geometry. Both the backing layer 510 and the wound pad 520 have substantially square shapes with rounded corners and is surrounded along its circumferential contour by the sealing ring 550 which is also provided with four straight edges interconnected by rounded corners. However, it should be understood that other geometrical shapes for the wound dressing are conceivable, such as other polygonal shapes, circular, oval, heart shapes or even irregular shapes.

Figure 6A:
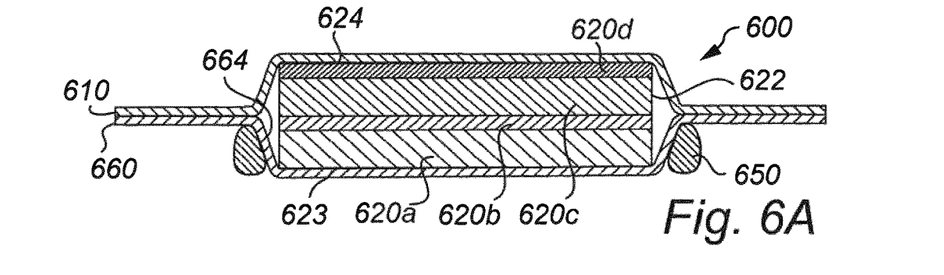
FIG. 6 depicts cross sections of exemplary wound dressings of the present disclosure having multilayered wound pads.
Figure 6B:
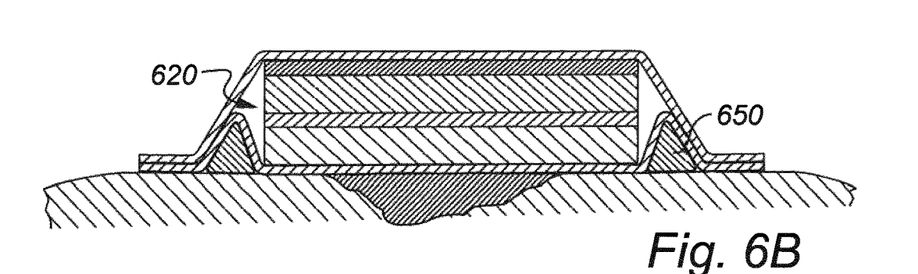
Figure 6C:
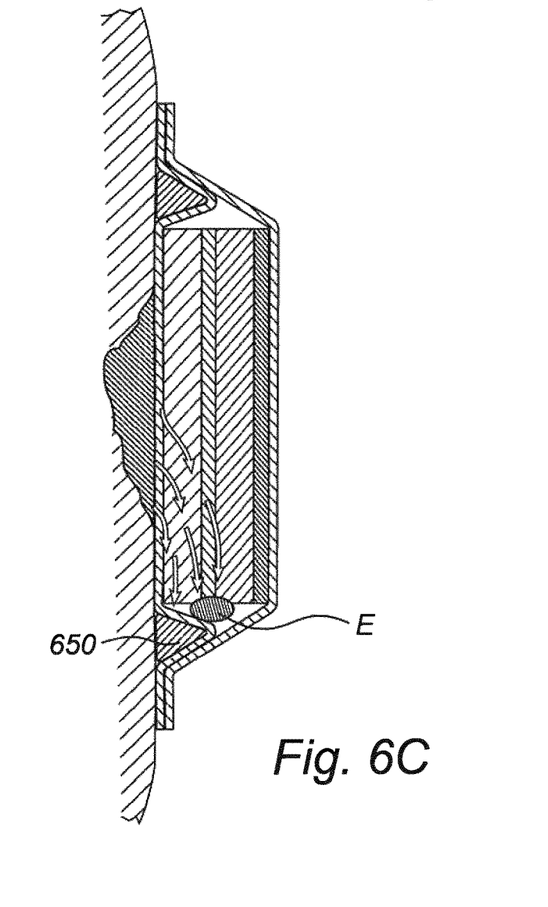

FIG. 6 depicts cross sections of exemplary wound dressings 600 of the present disclosure having multilayered wound pads 620. Similarly to the wound dressing in FIG. 4a, the wound dressing 600 in FIG. 6a comprises a backing layer 610 on a non-wound facing side 624 of the wound pad 620 and a wound contact layer 660 on a wound-facing side 623 of the wound pad 620. In at least this exemplary embodiment, the wound pad 620 comprises several layers having different properties and having been laminated together. The wound pad 620 comprises a first layer 620a on its wound-facing side 623, here illustrated as being in contact with the wound contact layer 660 (in particular a non-wound facing side 664 of the wound contact layer 660). The first layer 620a may be a lower absorbent and/or liquid-transporting layer (lower implying that it is intended to be closer to a wound than an upper layer). The first layer 620a is sandwiched between the wound contact layer 660 and a second layer 620b. The second layer 620b may be a lower liquid distributing layer which can act to spread liquid absorbed and transported by the first layer 620a in substantially radial directions (i.e. in directions towards the periphery 622 of the wound pad 620) and transmit the liquid to a third layer 620c. The third layer 620c may be an upper absorbent and/or liquid-transporting layer. The second layer 620b is thus sandwiched between the first layer 620a and the third layer 620c. The third layer 620c is in turn sandwiched between the second layer 620b and a fourth layer 620d of the wound pad 620. The fourth layer 620d may be an upper liquid distributing layer which can act to spread liquid absorbed and transported by the third layer 620c in substantially radial directions. The fourth layer 620d is sandwiched between the third layer 620c and the backing layer 610.

As can be seen in FIG. 6a a sealing ring 650 is attached to the wound contact layer 660, similarly as for the wound dressing in FIG. 4a. The function of the sealing ring 450 illustrated in FIG. 4B and 4C substantially corresponds to the function of the sealing ring 650 in FIGS. 6B and 6C.

FIG. 7 depicts an exemplary negative pressure wound treatment system 701 of the present disclosure. The system 701 comprises a negative pressure source 702 for providing negative pressure to a wound W and a wound dressing 700 of the inventive concept as described herein to be placed on the wound W. A conduit 703 is configured to transmit negative pressure from the negative pressure source 702 to the wound W. The illustrated wound dressing 700 comprises a backing layer 710, a wound pad 720 and a sealing ring 750, for instance, of the types illustrated in FIG. 5. The sealing ring 750 around the wound pad 720 of the wound dressing 700 provides an airtight seal, which is beneficial for negative pressure treatment.

EXAMPLES

Example 1

Method for Measuring the Softness/Penetration of Soft Silicone Gel

Figure 8A:
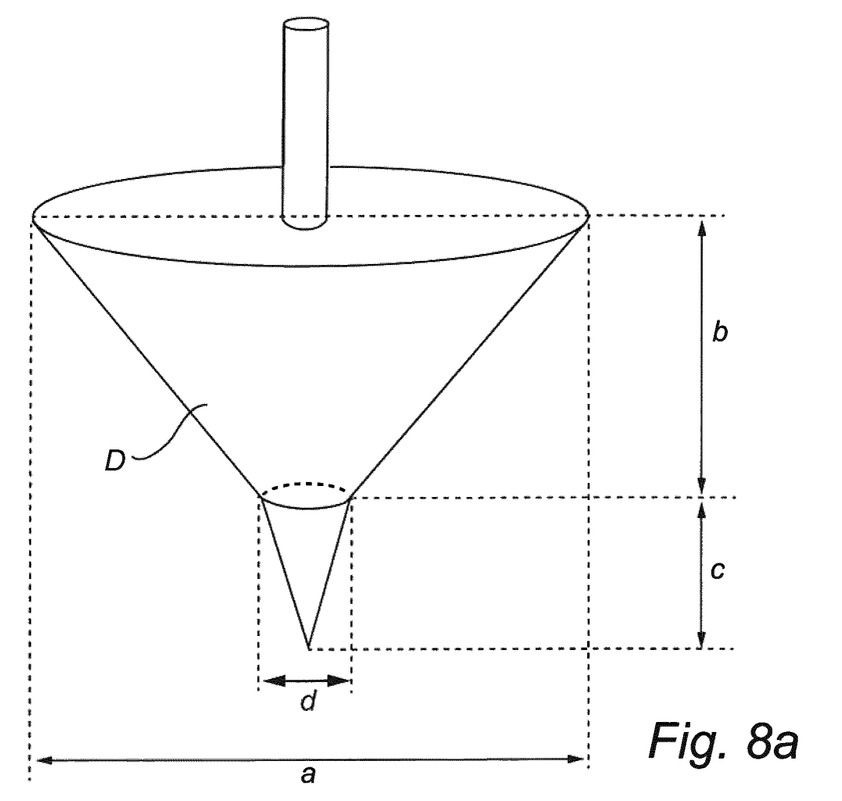
FIGS. 8a-b are schematic illustrations of a method for measuring softness of silicone gel.
Figure 8B:
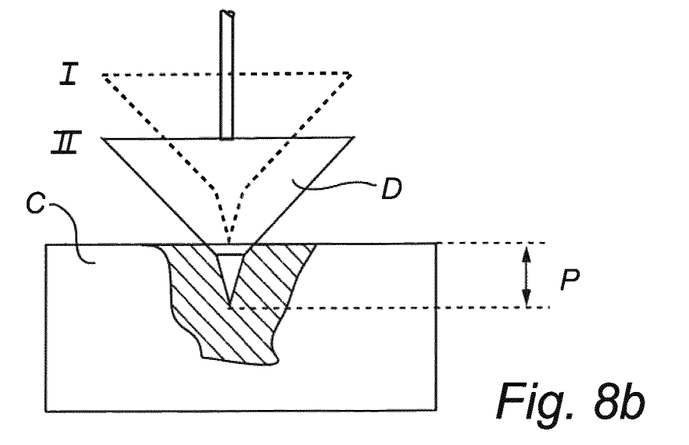

The method used for measuring the softness/ penetration of soft silicone gel is based on ASTM D 937 and DIN 51580, however deviates in a few steps which are explained below. FIGS. 8*a-b* illustrate this modified method for measuring softness in an adhesive by letting a cone D having a weight of 62.5 g penetrate a test specimen C by gravity, said specimen being made of the adhesive, the softness of which is to be determined, and having a thickness of 30 mm. The test specimen is obtained by filling a cylindrical container having an inner diameter of 60 mm and an inner height of 35-40 mm, with adhesive up to a height of 30 mm. When testing a silicone gel, uncured silicone prepolymers (e.g. A and B component of an RTV addition-cured silicone systems) are filled into the container, and this prepolymer mixture will then crosslink into a gel in the container. The prepolymer should be left to cure for at least 24 h at room temperature before measuring the softness/penetration. The cone used is shown in FIG. 8*a* and has the following measurements a=65 mm, b=30 mm, c=15 mm and d=8.5 mm. The method for determining softness includes lowering of the cone D to a position, indicated with dashed lines (see FIG. 8*b*), in which the tip of the cone just touches the surface of the test specimen C. The cone D is then released so that it is allowed to penetrate the test specimen C due to gravity. The extent of penetration, i.e. the distance by which the cone has penetrated the test specimen in mm is measured after 5 seconds, and represents the penetration value P (see FIG. 8*b*), which is larger, the softer the test specimen is. A penetrometer PNR 10 from Sommer & Runge K G, Germany, is used in the method. The method should be performed at standard laboratory conditions, e.g. at room temperature.

Example 2

Calibration of Softness/Penetration of Silicone Gel System

Five different mixtures (five replicates each) of the prepolymers (components A and B) of Wacker Silgel 612, all having different ratio of the A and B components, were prepared by mixing A and B in a cylindrical container having an inner diameter of 60 mm and an inner height of 35-40 mm, wherein the prepolymeric mixtures were added up to a height of 30 mm (as in Example 1). Subsequently, the prepolymeric mixtures were cured at room temperature for 24 h before measuring the softness (penetration depth) according to the method disclosed in Example 1. The results presented in Table 1 below were plotted (average penetration against ratio A:B) and fitted to a line using simple linear regression (graph not shown). Thereby, the resulting line or "calibration curve" can be used to determine which ratio of A and B that should be used to achieve a given/desirable softness of silicone gel. A new calibration curve should be done for each silicone gel system and/or each new batch of a silicone gel system used.

TABLE 1

| Silgel612 B | SilGel612 A | Penetration average | Penetration 1 | Penetration 2 | Penetration 3 | Penetration 4 | Penetration 5 |
|---|---|---|---|---|---|---|---|
| 100 | 105 | 17.424 | 17.44 | 17.44 | 17.53 | 17.22 | 17.49 |
| 100 | 110 | 15.522 | 15.41 | 15.54 | 15.56 | 15.64 | 15.46 |
| 100 | 120 | 11.322 | 11.37 | 11.43 | 11.19 | 11.35 | 11.27 |
| 100 | 130 | 8.148 | 8.05 | 8.23 | 8.16 | 8.19 | 8.11 |
| 100 | 140 | 5.842 | 5.77 | 5.81 | 5.73 | 5.9 | 6 |

Example 3

Preparation of Prototype and Testing Thereof

A prototype of a wound dressing of the present disclosure was made and tested for leakage. Silicone gel strips were made using a two-component RTV system (Wacker SilGel 612). The two components were mixed (A:B=114:100) such that the resulting silicone gel would have a softness of 14.8 mm (measured penetration depth, see method in Example 1 above), as calculated from the calibration curve, see Example 2. After mixing, the silicone mixture was poured onto a folded polyethylene-coated paper and left at room temperature to cure overnight. The polyethylene-coated paper was folded such that the profile of the resulting strips of silicone gel was equilateral triangular having a side of about 5 mm.

An island-type border dressing was prepared by attaching the none-adhesive side of a Mepilex® (Mölnlycke Health Care AB) (200×50 mm die cut from 50×20 cm product; thickness is ca. 5 mm) to the adhesive side of an Avance™ Film with Safetac® Technology (Molnlycke Health Care AB) (250×100 mm die cut from 20×27 cm product), Mepilex® being centered such that a border portion (25 mm) of said Avance™ Film surrounding the edges of Mepilex® was afforded.

Subsequently, the triangular silicone gel strips were pressed onto the wound-facing surface of the Avance™ Film with Safetac® Technology, along the entire lengths of, and directly adjacent to, all four edges of the rectangular-shaped wound pad (Mepilex®). The silicone gel strips were carefully applied such that no part of thereof was situated underneath the wound pad. These silicone gel strips adhered and remained adhered to the dressing.

The prepared dressing prototypes, with and without the silicone gel strips, were subsequently tested. Both dressings were placed on the knee caps of a voluntary human subject. The subject was in a sitting position with the knee at a 135 degree angle when the dressings were applied, but the subject was allowed to change positions during the testing period at will, thus resulting in the both dressings being bent and compressed when the subject was standing. The dressings were left in place and monitored for 20 hours (including sleeping). At the end of the 20-hour period, both dressings remained on the knee caps. However, air pockets had formed at the edges of the wound pad underneath the borders of the dressing without silicone gel strips. Such air pockets were not observed in the dressing with silicone gel strips.

Before removal, water (ca. 10 ml) coloured with red food colouring (Squires kitchen; QFC (Quality Food Color), with following ingredients: water, E129 colour, acetic acid (preservative)), was injected into the wound pad in the bottom edge area thereof (i.e. edge area closest to the foot). In order to detect leakage from the wound pad through the border, the water was injected from the backing of the wound pad with a syringe. The dressing prototype without silicone gel strips showed leakage through wrinkles/channels in the border and the skin was coloured where contact with coloured water had taken place. In contrast, the dressing prototype with silicone gel strips showed no leakage through visible wrinkles or channels, and no residuals of coloured water was seen on the skin upon removal. Thus, it can be concluded that the "seal ring" (silicone gel strips) works as predicted, and clearly demonstrates at least one advantage of the dressing according to the invention.

The above described various embodiments of the inventive wound dressing may suitably be sterilized and provided in a package. Suitably, the package is sealed and may have a sterile compartment in which the wound dressing is provided. It should therefore be understood that according to one aspect of the invention a product is provided, the product comprising a package containing a wound dressing according to anyone of the herein disclosed embodiments, including the embodiments disclosed in the claims.

Other embodiments of the invention will be apparent to those skilled in the art from a consideration of the specification or practice of the invention disclosed herein. It is intended that the specification and examples be considered as exemplary only, with the true scope of the invention being indicated by the following claims.

What is claimed is:

1. A wound dressing comprising:
   a backing layer;
   a wound pad having a wound-facing side extending in a first geometrical plane, a non-wound facing side extending in a second geometrical plane, and a circumferential contour;
   a sealing ring; and
   wherein
   the wound pad is affixed to the backing layer on the wound pad's non-wound facing side;
   the backing layer extends beyond the periphery of the wound pad;
   at least a portion of the sealing ring is disposed:
      between said first and said second plane,
      within a distance of 5 mm from the contour of the wound pad, and
      continuously along the contour of the wound pad, and
   the backing layer extends beyond the periphery of the sealing ring,
   a wound contact layer having a wound-facing side and an opposing non wound-facing side, wherein the wound pad is disposed between the backing layer and the wound contact layer; and the wound contact layer extends beyond the periphery of the wound pad, wherein the sealing ring is attached to the wound-facing side of the wound contact layer.

2. The wound dressing of claim 1, wherein a portion of the wound dressing extending beyond the periphery of the wound pad defines a border, wherein a cross-section of the sealing ring extends from the border to or beyond said first geometrical plane.

3. The wound dressing of claim 1, wherein the height of the sealing ring is the same as, or larger than, the distance between said first and said second geometrical plane.

4. The wound dressing of claim 1, wherein a thickness of the sealing ring is equal to or smaller than the height of the sealing ring.

5. The wound dressing of claim 4, wherein the thickness of the sealing ring is less than 70% of the height of the sealing ring.

6. The wound dressing of claim 1, wherein the backing layer is coated with an adhesive at least on parts of the backing layer that extend beyond the periphery of the sealing ring.

7. The wound dressing of claim 1, wherein the wound contact layer is perforated.

8. The wound dressing of claim 1, wherein the wound contact layer is coated with an adhesive at least on the parts of the wound contact layer that extend beyond the periphery of the sealing ring.

9. The wound dressing of claim 1, wherein the thickness of the sealing ring is 30-100% of the height of the sealing ring.

10. The wound dressing of claim 1, wherein the height of the sealing ring corresponds to half the thickness of the wound pad.

11. The wound dressing of claim 1, wherein the sealing ring is hydrophobic.

12. The wound dressing of claim 1, wherein the sealing ring comprises or consists of a silicone gel.

13. The wound dressing of claim 1, wherein the wound pad is a multilayered wound pad.

14. The wound dressing of claim 1, wherein said at least a portion of the sealing ring is disposed within 4 mm of the contour of the wound pad.

15. The wound dressing of claim 1, wherein the sealing ring is disposed immediately adjacent to the contour of the wound pad.

16. The wound dressing of claim 1, further comprising a port in the backing layer that allows fluid communication between the wound dressing and a conduit connected to the port.

17. A negative pressure wound treatment system comprising:
   a negative pressure source for providing negative pressure to a wound;
   a wound dressing in accordance with claim 1; and
   a conduit configured to transmit negative pressure from the negative pressure source to the wound dressing.

* * * * *